United States Patent [19]

Vecchietti et al.

[11] Patent Number: 5,030,649
[45] Date of Patent: Jul. 9, 1991

[54] 2-AMINOETHYLAMINE DERIVATIVES, COMPOSITIONS OF THE SAME AND USE OF SAID COMPOUNDS IN MEDICINE

[75] Inventors: Vittorio Vecchietti; Giuseppe Giardina, both of Baranzate, Italy

[73] Assignee: Dr. Lo. Zambelletti S.p.A., Italy

[21] Appl. No.: 598,825

[22] Filed: Oct. 16, 1990

Related U.S. Application Data

[63] Continuation of Ser. No. 98,327, Sep. 17, 1987, abandoned.

[30] Foreign Application Priority Data

Sep. 17, 1986 [GB] United Kingdom ............... 8622352
Dec. 17, 1986 [GB] United Kingdom ............... 8630113

[51] Int. Cl.$^5$ .................... A61K 31/40; C07D 295/04
[52] U.S. Cl. .................... 514/428; 548/567; 548/568
[58] Field of Search ............... 514/428; 548/567, 568

[56] References Cited

U.S. PATENT DOCUMENTS

| | | | |
|---|---|---|---|
| 3,103,516 | 9/1963 | Schmitt et al. | 260/294 |
| 4,753,952 | 6/1988 | Vecchietti et al. | 514/307 |
| 4,801,585 | 1/1989 | Vecchietti et al. | 514/210 |

FOREIGN PATENT DOCUMENTS

| | | |
|---|---|---|
| 0017376 | 10/1980 | European Pat. Off. |
| 0122018 | 10/1984 | European Pat. Off. |
| 0176309 | 4/1986 | European Pat. Off. |
| 0254545 | 1/1988 | European Pat. Off. |
| 254545 | 1/1988 | European Pat. Off. |
| 1112514 | 8/1961 | Fed. Rep. of Germany . |
| 2091250 | 7/1982 | United Kingdom . |
| 2096607 | 10/1982 | United Kingdom . |

OTHER PUBLICATIONS

Aboskalova et al, Chem. Abstr. 91 (1979), 56751s.

*Primary Examiner*—Joseph Paul Brust
*Attorney, Agent, or Firm*—Rosenman & Colin

[57] ABSTRACT

A compound of formula (I):

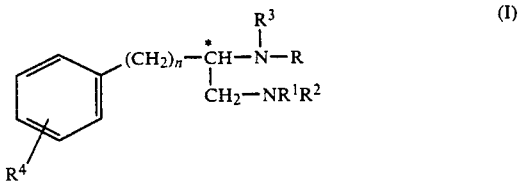

or a salt and/or solvate thereof, wherein
R represents an acyl group containing a substituted or unsubstituted carbocyclic aromatic or heterocyclic aromatic group;
$R^1$ and $R^2$ each independently represents an alkyl, alkenyl or alkynyl group or $R^1$ together with $R^2$ represents a $C_{3-6}$ polymethylene or alkenylene group;
$R^3$ represents hydrogen or alkyl;
$R^4$ represents hydrogen, halogen, alkyl, hydroxy, alkoxy, nitrile, nitro, amino or mono or disubstituted amino; and
n represents 0 or an integer 1,
is useful in the treatment of pain.

13 Claims, No Drawings

2-AMINOETHYLAMINE DERIVATIVES, COMPOSITIONS OF THE SAME AND USE OF SAID COMPOUNDS IN MEDICINE

This application is a continuation of U.S. application Ser. No. 07/098,327, filed Sept. 17, 1987, now abandoned.

This invention is concerned with 2-amino ethylamine derivatives, to processes for the preparation of such compounds, to compositions containing them, and to the use of such compounds and compositions in medicine.

Compounds which are K-receptor agonists act as analgesics through interaction with Kappa opioid receptors. The advantage of K-receptor agonists over the classical u-receptor agonists, such as morphine, lies in their ability of causing analgesia while being devoid of morphine-like behavioural effects and addiction liability.

We have now discovered a novel class of 2-amino ethylamine derivatives which exhibit K-receptor agonism without the behavioural effects of morphine and morphine analogues, and which are thus of potential therapeutic utility as analgesics.

Accordingly, the present invention provides a compound of formula (I):

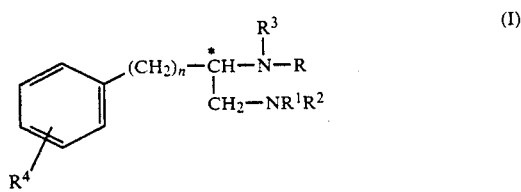

or a salt and/or solvate thereof, wherein
R represents an acyl group containing a substituted or unsubstituted carbocyclic aromatic or heterocyclic aromatic group;
$R^1$ and $R^2$ each independently represents an alkyl, alkenyl or alkynyl group or $R^1$ together with $R^2$ represents a $C_{3-6}$ polymethylene or alkenylene group;
$R^3$ represents hydrogen or alkyl;
$R^4$ represents hydrogen, halogen, alkyl, hydroxy, alkoxy, nitrile, nitro, amino or mono or disubstituted amino; and
n represents 0 or an integer 1.

The group R preferably has the formula (II)

$$-CO-(CH_2)_a-X-Ar \qquad (II)$$

in which
a is 0 or an integer 1, 2 or 3
X is a direct bond, or O, S or $NR^6$ in which $R^6$ is hydrogen or $C_{1-6}$ alkyl, and
Ar is a substituted or unsubstituted carbocyclic aromatic or heterocyclic aromatic group.

Suitable substituents for the carbocyclic or heterocyclic group include up to 5, preferably up to 3 of the groups selected from alkyl, aryl, aralkyl, hydroxy, alkoxy, or an electron withdrawing group and wherein at least one pair of the substituents may together form a carbocyclic ring. Suitable electron withdrawing groups include halogen, a trifluoromethyl, a nitro, or cyano group or $-SO_3H$, $-SO_2NR^7R^8$, $-CO_2R^7$, $-COR^7$ or $-CONR^7R^8$ wherein $R^7$ and $R^8$ each independently represents hydrogen, alkyl or aryl.

Preferably Ar is substituted or unsubstituted phenyl or substituted or unsubstituted thienyl.

X is typically oxygen or a direct bond, and a is typically 0 or 1.

When used herein, the term 'carbocyclic aromatic group' includes single or fused rings of carbon atoms, preferably having 5 to 12 carbon atoms, optionally substituted as described hereinbefore; carbocyclic aromatic rings may be optionally substituted phenyl and napthyl rings.

When used herein the term 'heterocyclic aromatic group' includes single or fused rings comprising up to four hetero atoms in the or each ring selected from oxygen, nitrogen and sulphur, the rings being optionally substituted as described hereinbefore.

When used herein the term 'alkyl' or 'alk' (in, for example, alkoxy) relates to straight or branched chains containing for example up to 12 carbon atoms, suitably from 1 to 6 carbon atoms.

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl $C_{1-6}$ alkylcarbonyloxy, or $C_{1-6}$ alkylcarbonyl groups.

The term 'halogen' refers to fluorine, chlorine, bromine and iodine.

In one suitable aspect R represents a moiety of formula (III):

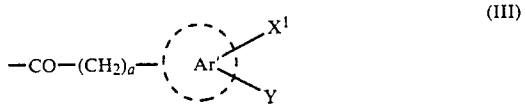

wherein Ar' represents a phenyl group or a 2- or 3-thienyl group, $X^1$ and Y each independently represent hydrogen, alkyl, aryl, aralkyl, hydroxy, alkoxy, halogen, a trifluoromethyl, a nitro, or cyano group or $-SO_3H$, $SO_2NR^7R^8$, $-CO_2R^7$, $-COR^7$ or $-CONR^7R^8$ wherein $R^7$ and $R^8$ are as defined above or $X^1$ together with Y form a cycloalkylene ring; and a represents an integer 1, 2, or 3.

Suitably, $X^1$ and Y independently represent hydrogen, halogen, trifluoromethyl or nitro.

Suitable examples of R are:

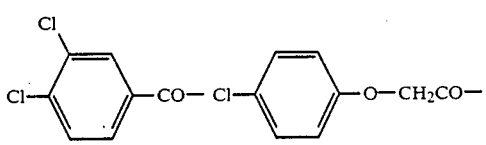

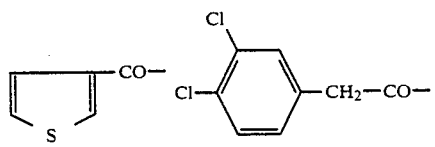

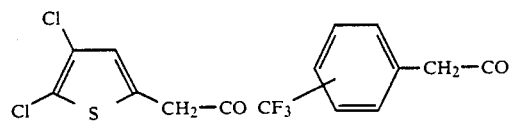

When representing an alkyl group, $R_1$ and $R_2$ may each independently be a methyl, ethyl, propyl, butyl, pentyl or hexyl group, and preferably a methyl group.

When representing a polymethylene group, $R_1$ together with $R^2$ may represent propylene, butylene, pentylene or hexylene, and preferably represent butylene. When representing an alkylene group, $R^1$ together with $R^2$ may represent —CH$_2$—CH=CH—CH$_2$—.

Preferably, $R^3$ represents an alkyl group, such as methyl, ethyl, propyl, butyl, pentyl or hexyl.

Suitably, $R^4$ represents hydrogen, halogen, such as chlorine or bromine, or alkyl such as methyl, ethyl, propyl, butyl, pentyl or hexyl.

In a particularly preferred aspect the present invention provides a compound selected from the group consisting of:

(S)-N-methyl-N-[2-[1-(1-pyrrolidinyl)-2-phenyl]ethyl]-3,4-dichlorobenzene acetamide;

(S)-N-methyl-N-[2-(1-dimethylamino-2-phenyl)ethyl]-3,4-dichlorobenzene acetamide;

(S)-N-ethyl-N-[2-(1-dimethylamino-2-phenyl)ethyl]-3,4-dichlorobenzene acetamide;

(S)-N-methyl-N-[2-(1-dimethylamino-3-phenyl)propyl-3,4-dichlorobenzene acetamide;

(S)-N-methyl-N-[2-[1-(1-pyrrolidinyl)-3-phenyl]-propyl]-3,4-dichlorobenzene acetamide;

(S)-N-methyl-N-[2-[1-(1-pyrrolidinyl)-2-phenyl]-ethyl]-O-nitrobenzene acetamide;

(S)-N-methyl-N-[2-[1-dimethylamino-2-phenyl]ethyl]-o-nitrobenzene acetamide;

(S)-N-methyl-N-[2-[1-(1-pyrrolidinyl)-2-phenyl]-ethyl]-m-nitrobenzene acetamide;

(S)-N-methyl-N-[2-(1-dimethylamino-2-phenyl)ethyl]-m-nitrobenzene acetamide;

(S)-N-methyl-N-[2-[1-(1-pyrrolidinyl)-2-phenyl]ethyl]-p-nitrobenzene acetamide;

(S)-N-methyl-N-[2-(1-dimethylamino-2-phenyl)ethyl]-p-nitrobenzene acetamide;

(S)-N-methyl-N-[2-[1-(1-pyrrolidinyl)-2-phenyl]ethyl]-p-trifluoromethylbenzene acetamide;

(S)-N-methyl-N-[2-(1-dimethylamino-2-phenyl)ethyl]-p-trifluoromethylbenzene acetamide;

(S)-N-methyl-N-[2-[1-(1-pyrrolidinyl)-2-phenyl]ethyl]-m-trifluoromethylbenzene acetamide;

(S)-N-methyl-N-[2-(1-dimethylamino-2-phenyl)ethyl]-m-trifluoromethylbenzene acetamide hydrochloride;

(S)-N-methyl-N-[2-[1-(1-pyrrolidinyl)-2-phenyl]ethyl]-2-(5,6,7,8-tetrahydro-2-naphthyl)acetamide;

(S)-N-methyl-N-[2-(1-dimethylamino-2-phenyl)ethyl]-2-(5,6,7,8-tetrahydro-2-naphthyl)acetamide;

or a salt, preferably a hydrochloride, and/or a solvate thereof, preferably a hydrate.

The compounds of formula (I) or their salts and/or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula (I) include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

A preferred salt is the hydrochloride.

Examples of a pharmaceutically acceptable solvate of a compound of formula (I) includes a hydrate of a compound of formula (I).

The compounds of formula (I) have at least one asymmetric centre and therefore exist in more than one stereoisomeric form. The invention extends to all such forms and to mixtures thereof, including racemates.

A preferred stereoisomeric form is that wherein the carbon atom marked with an asterisk in formula (I) is in the (S)-configuration.

The present invention also provides a process for preparing a compound of formula (I), or a salt and/or solvate thereof, which process comprises reacting a compound of formula (IV):

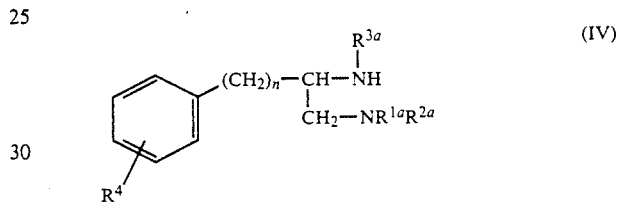

wherein $R^4$ is as defined in relation to formula (I) or is a protected form thereof, n is as defined in relation to formula (I), $R^{1a}$ is $R^1$ or a moiety convertible to $R^1$, $R^{2a}$ is $R^2$ or a moiety convertible to $R^2$ and $R^{3a}$ is $R^3$ or a moiety convertible to $R^3$;

with a compound of formula (V):

$$R^a\text{—OH} \qquad (V)$$

or an active derivative thereof, wherein $R^a$ represents R, as defined in relation to formula (I), or a moiety convertible to R; and thereafter if required carrying out one or more of the following optional steps:

i) removing any protecting group;

ii) where $R^{1a}$ is other than $R^1$, converting $R^{1a}$ to $R^1$ and/or where $R^{2a}$ is other than $R^2$, converting $R^{2a}$ to $R^2$ and/or where $R^{3a}$ is other than $R^3$, converting $R^{3a}$ to $R^3$;

iii) where $R^a$ is other than R, converting $R^a$ to R;

iv) converting a compound of formula (I) to a further compound of formula (I);

v) preparing a salt and/or solvate of the compound of formula (I) so formed.

Suitable active derivatives of the compound of formula (V) are acid chlorides or acid anhydrides. Another suitable derivative is a mixed anhydride formed between the acid and an alkyl chloroformate.

For example, in standard methods well known to those skilled in the art, the compound of formula (IV) may be reacted with a compound of formula (V), wherein the compound of formula (V) is:

a) an acid chloride, the reaction being carried out in the presence of an inorganic or organic base, b) an acid, the reaction being carried out in the presence of dicyclohexyl carbodiimide, N-dimethylaminopropyl-N'-ethyl carbodiimide or carbonyl diimidazole, or c) a mixed anhydride generated in situ from the acid and an alkyl (for example ethyl)chloroformate.

Suitably when $R^{3a}$ is other than $R^3$, $R^{3a}$ represents a protecting group or a moiety which is reducible to a group $R^3$.

Typical protecting groups $R^{3a}$ are benzyl groups or substituted benzyl groups.

A typical moiety reducible to an alkyl group $R^3$ is a moiety of formula $-CO-R^9$ wherein $R^9$ represents hydrogen or an alkyl group such that $-CH_2R^9$ represents the alkyl group $R^3$ or, for compounds wherein $R^3$ is methyl, a leaving group such as a benzyloxy group.

It will be appreciated that, certain protecting groups such as benzyl groups may also be removed under reducing conditions and hence such protecting groups fall into either category of suitable variables $R^3$.

When $R^{1a}$ or $R^{2a}$ are other than $R^1$ or $R^2$, suitable values for $R^{1a}$ and $R^{2a}$ are those indicated above for $R^{3a}$ when $R^{3a}$ is other than $R^3$.

A compound of formula (I) may be converted into a further compound of formula (I), by interconversion of suitable substituents. Thus certain compounds of formula (I) are useful intermediates in forming other compounds of the present invention.

For example:

(i) when $R^3$ represents an alkyl group, it may be converted to $R^3$ representing a hydrogen atom by conventional amine dealkylation such as for example when $R^3$ is benzyl or substituted benzyl by conventional catalytic hydrogenation;

(ii) when $R^3$ represents hydrogen, it may be converted to $R^3$ representing an alkyl group by conventional amine alkylation; and (iii) when $R^1$ or $R^2$ or $R^3$ represent alkyl groups they may be converted to different alkyl groups by conventional dealkylation, protection and alkylation steps.

A compound of formula (IV) may be prepared by reducing a compound of formula (VI):

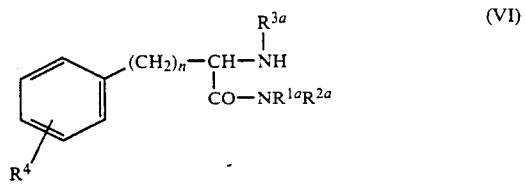

wherein $R^{1a}$, $R^{2a}$, $R^{3a}$, $R^4$ and n are as defined in relation to formula (IV), and thereafter if required carrying out one or more of the following optional steps:

(i) removing any protecting group;

(ii) where $R^{1a}$ is other than $R^1$, converting $R^{1a}$ to $R^1$ and/or where $R^{2a}$ is other than $R^2$, converting $R^{2a}$ to $R^2$, and/or where $R^{3a}$ is other than $R^3$, converting $R^{3a}$ to $R^3$;

(iii) converting a compound of formula (IV) into a further compound of formula (IV).

Suitably, in the preceding reaction when $R^{1a}$, $R^{2a}$ or $R^{3a}$ in formula (VI) represents a moiety reducible to $R^1$, $R^2$ or $R^3$ respectively, the optional step (ii) may be carried out at the same time as the reduction of the $-CO-$ group in the moiety $-(CH_2)_n-CH-CO-$ of formula (VI).

The conversions of $R^{1a}$ to $R^1$, $R^{2a}$ to $R^2$, $R^{3a}$ to $R^3$ and a compound of formula (IV) to a further compound of formula (IV) may be carried out by using analogous procedures to those used for the compounds of formula (I), The reduction of a compound of formula (VI) may be carried out under conventional reducing conditions, for example by using a complex metal hydride reducing agent, especially lithium aluminium hydride, in an aprotic solvent, such as diethylether or tetrohydrofuran, at low to elevated temperatures, conveniently at ambient temperature.

A compound of formula (VI) may be prepared from a compound of formula (VII):

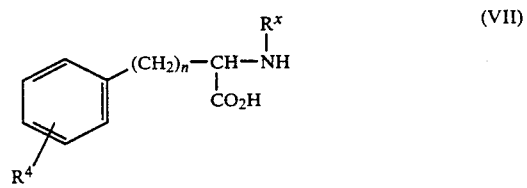

wherein $R^4$ and n are as defined in relation to formula (IV), and $R^x$ represents a protecting group or a group $R^{3a}$ as defined in relation to formula (IV); by reaction with a compound of formula (VIII):

wherein $R^{1a}$ and $R^{2a}$ are as defined in relation to formula (IV) and X represents hydrogen or a leaving group; and thereafter if required carrying out one or more of the following optional steps:

(i) removing any protecting group;

(ii) where $R^{1a}$ is other than $R^1$, converting $R^{1a}$ to $R^1$ and/or where $R^{2a}$ is other than $R^2$, converting $R^{2a}$ to $R^2$, and/or where $R^{3a}$ is other than $R^3$, converting $R^{3a}$ to $R^3$;

(iii) where $R^x$ represents a protecting group, converting $R^x$ to a group $R^{3a}$.

The reaction between compounds of formulae (VII) and (VIII) may be carried out under conventional peptide bond forming conditions, for example in the presence of dicyclohexylcarbodi-imide in any suitable aprotic solvent, such as dimethylformamide or a methylene dichloride, at low to elevated temperatures, conveniently at ambient temperature.

The compounds of formula (VII) and (VIII) are either known compounds or may be prepared using methods analogous to those used to prepare known compounds.

The compounds of formula (IV) may also be prepared from a compound of formula (IX):

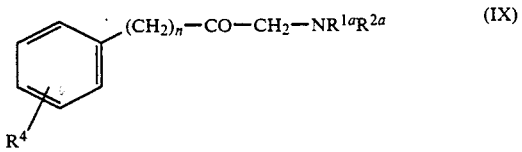

wherein $R^{1a}$, $R^{2a}$, $R^4$ and n are as defined in relation to formula (IV), by reducing the compound of formula (IX) in the presence of an amine of formula (X):

wherein $R^{3a}$ is as defined in relation to formula (IV). and thereafter if required carrying out one or more of the following optional steps:
(i) removing any protecting group;
(ii) where $R^{1a}$ is other than $R^1$, converting $R^{1a}$ to $R^1$ and/or where $R^{2a}$ is other than $R^2$, converting $R^{2a}$ to $R^2$.

The preceding reaction may be carried out under conventional reductive amination conditions.

The compounds of formula (IX) and (X) are either known compounds or they may be prepared using methods analogous to those used to prepare known compounds.

For compounds of formula (I) wherein $R^{3a}$ represents methyl a suitable reaction pathway is that shown below in Scheme (I):

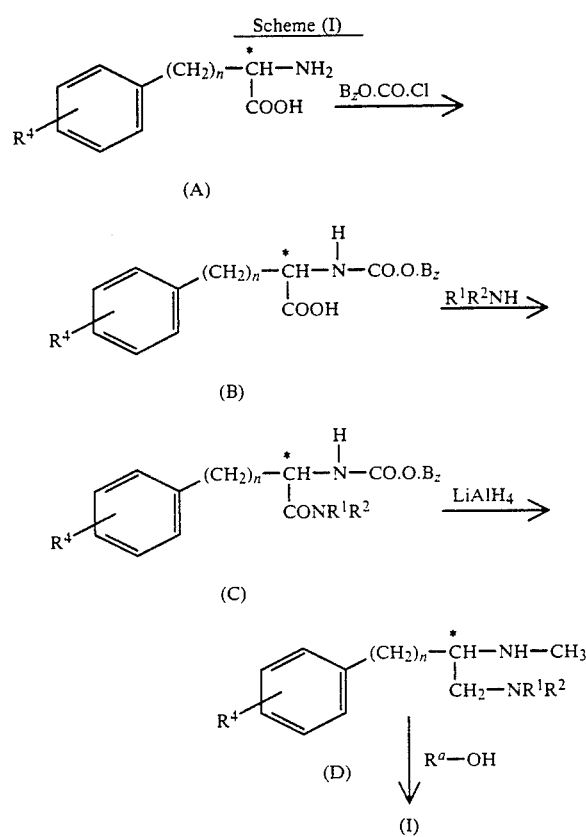

wherein $R^1$, $R^2$, $R^4$, $R^a$ and n are as defined in relation to formula (I). Thus when $R^4 = H$ and $n = 1$ the amino acid (A) is phenylglycine or when $R^4 = H$ and $n = 1$ the aminoacid (A) is phenylalanine.

For compounds of formula (I) wherein $R^{3a}$ represents an alkyl group other than methyl, a suitable reaction pathway is that shown below in Scheme (II):

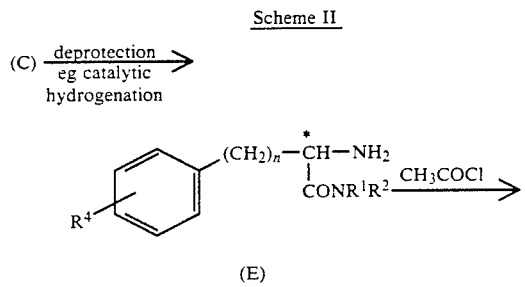

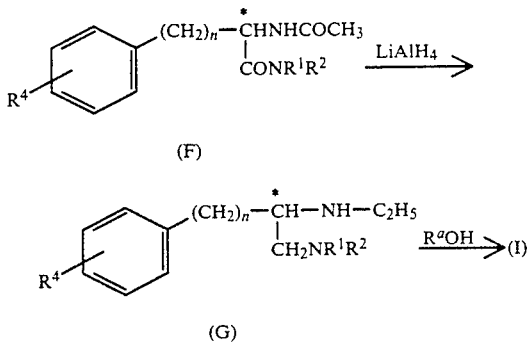

wherein formula (C) is as defined in Scheme (I) and $R^1$, $R^2$, $R^4$, $R^a$ and n are as defined in relation to formula (I).

The compounds of formula (I) may be converted into their pharmaceutically acceptable acid addition salts by reaction with the appropriate organic or mineral.

Solvates of the compounds of formula (I) may be formed by crystallization or recrystallization from the appropriate solvent. For example hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

The compounds of formula (I) exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form. For example routes analogous to Scheme (I) or (II) above do not involve an inversion of configuration of the asterisked carbon of the starting amino acid. Hence an amino acid whereon the asterisked carbon has the S-configuration provides a compound of formula (I) wherein the asterisked carbon has the S-configuration.

The activity of the compounds of formula (I) or the pharmaceutically acceptable salts and/or solvates thereof in standard analgesic tests indicates that they are of therapeutic utility in the treatment of pain.

Accordingly the present invention also provides a compound of formula (I), or a pharmaceutically acceptable salt and/or solvate thereof, as an active therapeutic substance.

The present invention further provides a pharmaceutical composition comprising a compound of formula (I), or a pharmaceutically acceptable salt and/or solvate thereof, and a pharmaceutically acceptable carrier therefor.

The present invention also provides the use of a compound of formula (I), or a pharmaceutically acceptable salt or solvate thereof, for the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water of normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as apoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

The present invention also provides a method of treating pain in mammals, particularly in humans, which comprises administering an effective non-toxic amount of a pharmaceutically acceptable compound of formula (I) or a pharmaceutically acceptable salt and/or solvate thereof or composition thereof to a sufferer. No toxic effects are indicated for the above defined pharmaceutically acceptable compounds of the invention, in the abovementioned dosage ranges.

Compounds of this invention and their preparation are illustrated in the following Examples.

EXAMPLE 1

(S)-N-methyl-N-[1-phenyl-2-(pyrrolidin-1-yl)]ethyl-3,4-dichlorophenylacetamide hydrochloride 3.2 g of(S)-N-methyl-1-phenyl-2-(1-pyrrolidinyl)-ethanamine (15.6 mmoles) and 4.5 g of 3,4-dichlorophenylacetic acid (22 mmoles) are dissolved in 80 ml of methylene chloride. 6.4 g of dicyclohexylcarbodiimide (31 mmoles), dissolved in the minimum amount of methylene chloride, are dropped into this solution kept at 0°-5° C. The reaction mixture is allowed to come to room temperature and stirred for 6 hours. The precipitated dicyclohexylurea is filtered off, and the solution evaporated in-vacuo to dryness.

The residual oil is treated with 10 ml of HCl 10% and 10 ml ethanol. A small amount of precipitated solid is filtered off, the solution is evaporated in-vacuo, and the residue is partitioned between 36% NaOH solution and ethyl acetate. The organic solution is dried on sodium sulphate and evaporated to dryness. The oily residue is dissolved in 50 ml of acetone and the solution brought to slightly acidic pH with HCl/diethyl ether. The precipitate is filtered, washed with acetone and ether, and dried.

Yield 2.8 g; $C_{21}H_{25}Cl_3N_2O$; M.P.=240° C.; M.W.=427.798; $[\alpha]_D=+23.64$ (C=1, MeOH).

The elemental analysis and NMR spectrum confirmed the structure of the compound.

EXAMPLE 2

(S)-N-methyl-N-(1-phenyl-2-dimethylamino)ethyl-3,4-dichlorophenylacetamide hydrochloride 2.6 g. of (S)—$N_1$, $N_2$, $N_2$—trimethyl-1-phenyl ethanediamine (14.70 mmoles) and 3.7 g. of 3,4-dichlorophenylacetic acid (18.0 mmoles) are dissolved in 80 ml of dry methylene chloride. 5.0 g. of dicyclohexylcarbodiimide (24.30 mmoles), dissolved in 20 ml of methylene chloride, are dropped into this solution kept at 0° C. The reaction mixture is allowed to come to room temperature and stirred for 6 hours. The precipitated dicyclohexylurea is filtered off, and the solution evaporated in-vacuo to dryness.

The residual oil is treated with 10 ml of HCl 10% and 10 ml of ethanol. A small amount of precipitated solid is filtered off, the solution is evaporated in-vacuo and the residue is partitioned between 36% NaOH solution and ethyl acetate. The organic solution is dried on sodium sulphate and evaporated to dryness. The oily residue is dissolved in 50 ml of acetone and the solution brought to acid pH with HCl/diethyl ether. The precipitate is filtered, washed and dried.

Yield 1.0 g; $C_{19}H_{23}Cl_3N_2O$; M.P.=225° C.; M.W.=401.761; $[\alpha]_D^{20}=+104.77$ (C=1, MeOH).

Elemental analysis: Calcd. C, 56.80; H, 55.77; N, 6.97; Cl, 26.47; Found C, 56.63; H, 5.76; N, 6.94; Cl, 26.35.

I.R. (KBr): 1650 cm$^{-1}$ (s)

| $^1$H N.M.R. (CDCl$_3$): | $\delta$ 12.0 | s 1 H |
|---|---|---|
| | $\delta$ 7.0–7.5 | m 8 H |
| | $\delta$ 6.4 | dd 1 H |
| | $\delta$ 2.8–4.4 | m 13 H |

EXAMPLE 3

(S)-N-ethyl-N-(1-phenyl-2-dimethylamino)ethyl-3,4-dichlorophenylcetamide hydrochloride 700 mg. of (S) $N_1$-ethyl-$N_2$, $N_2$-dimethyl-1-phenyl ethanediamine (3.64 mmoles) and 1.5 g. of 3,4-dichlorophenylacetic acid (7.31 mmoles) are dissolved in 50 ml of dryed methylene chloride. 2.5 g. of dicyclohexylcarbodiimide (12.10 mmoles), dissolved in 10 ml of methylene chloride, are dropped into this solution kept at 0° C. The reaction mixture is allowed to come to room temperature, stirred for 6 hours and left at rest overnight. The precipitated dicyclohexylurea is filtered off, and the solution evaporated in-vacuo to dryness.

The residue is treated with 10 ml of HCl 10% and 10 ml ethanol. A small amount of precipitated solid is filtered off and the solution is evaporated in-vacuo; the residue is partitioned between 36% NaOH solution and ethyl acetate. The organic solution is dried on sodium sulphate and evaporated to dryness. The oily residue is dissolved in 25 ml of acetone and the solution brought to slightly acid pH with HCl/diethyl ether. The precipitate is filtered, washed with acetone and dried.

Yield 400 mg. $C_{20}H_{25}Cl_3N_2O$; M.P.=195°–200° C.; M.W.=415.787; $[\alpha]_D^{20}=+70.8$ (C=1, MeOH).

Elemental analysis: Calcd. C, 57.77; H, 6.06; N, 6.74; Cl, 25.56; Found C, 57.38; H, 6.01; N, 6.69; Cl, 25.22.

I.R. (KBr): 1660 cm$^{-1}$ (s)

| $^1$H N.M.R. (CDCl$_3$): | $\delta$ 12.0 | s 1 H |
|---|---|---|
| | $\delta$ 7.0–7.5 | m 8 H |
| | $\delta$ 6.0–6.2 | dd 1 H |
| | $\delta$ 2.8–4.1 | m 12 H |
| | $\delta$ 0.7–0.9 | t 3 H |

EXAMPLE 4

(S)-N-methyl-N-[(1-dimethylamino-3-phenyl)prop-2-yl]-3,4-dichlorophenylacetamide hydrochloride 2.4 g. of N-methyl-(1-dimethylamino-3-phenyl)propyl-2-amine (12.5 mmoles and 2.8 g. of dichlorophenylacetic acid (13.66 mmoles) are dissolved in 70 ml of dry methylene chloride. 5.8 g. of dicyclohexylcarbodiimide (28.15 mmoles), dissolved in 30 ml of methylene chloride, are dropped into this solution kept at 0° C. The reaction mixture is allowed to come to room temperature, stirred for 6 hours and left at rest overnight. The precipitated dicyclohexylurea is filtered off and the solution evaporated in-vacuo to dryness.

The residual oil is treated with 10 ml of HCl 10% and 10 ml of ethanol. A small amount of precipitated solid is filtered off, the solution evaporated in-vacuo and the residue is partitioned between 36% NaOH solution and ethyl acetate.

The organic solution is dried on sodium sulphate and evaporated to dryness.

The residual oil is dissolved in 50 ml of acetone and the solution brought to acidic pH wit HCl/diethyl ether.

The precipitate is filtered, washed and dried.

Yield 1.2 g; $C_{20}H_{25}Cl_3N_2O$; M.P.=175° C.; M.W.=415.787; $[\alpha]_D^{20}=-4.65$ (C=1, MeOH).

Elemental analysis: Calcd. C, 57.77; H, 6.06; N, 6.74; Cl, 25.58; Found C, 57.51; H, 6.03; N, 6.68; Cl, 25.76.

I.R. (KBr): 1640 cm$^{-1}$ (s)

| $^1$H N.M.R. (CDCl$_3$): | $\delta$ 11.9 | s 1 H |
|---|---|---|
| | $\delta$ 6.8–7.3 | m 8 H |
| | $\delta$ 5.1–5.6 | m 1 H |
| | $\delta$ 3.3–4.0 | m 2 H |
| | $\delta$ 2.4–3.0 | m 13 H |

EXAMPLE 5

(S)-N-methyl-N-[[1-(pyrrolidin-1-yl)-3-phenyl]prop-2-yl]-3,4-dichlorophenylacetamide hydrochloride 2.2 g. of (S)-N-methyl-[1-(1-pyrrolidinyl)-3-phenyl]-propyl-2-amine (10.10 mmoles) and 2.6 g. of 3,4-dichlorophenylacetic acid (12.70 mmoles) are dissolved in 50 ml of methylene chloride. 4.0 g. of dicyclohexylcarbodiimide (19.40 mmoles), dissolved in 20 ml of dry methylene chloride, are dropped into this solution kept at 0° C. The reaction mixture is allowed to come to room temperature, stirred for 6 hours and left at rest overnight. The precipitated dicyclohexylurea is filtered off and the solution evaporated in-vacuo to dryness.

The residual oil is treated with 10 ml of HCl 10% and 10 ml of ethanol. A small amount of precipitated solid is filtered off, the solution evaporated in-vacuo and the residue is partitioned between 36% NaOH solution and ethyl acetate. The organic solution is dried on sodium sulphate and evaporated to dryness. The residual oil is chromatographed on silica gel, eluting with $CH_2Cl_2/1-6\%$ MeOH, to afford 1.5 g. of pure product, which is dissolved in 50 ml of ethyl acetate and the solution brought to acidic pH with HCl/diethyl ether. The precipitate is filtered, washed and dried.

Yield 1.3 g. $C_{22}H_{27}Cl_3N_2O$; M.P.=187°-190° C.; M.W.=441.823; $[\alpha]_D^{20}=+4.22$ (C=1, MeOH).

I.R. (KBr): 1640 $cm^{-1}$ (s)

| $^1$H N.M.R. (CDCl$_3$): | δ 12.0 | s 1 H |
|---|---|---|
| | δ 6.9-7.4 | m 8 H |
| | δ 5.2-5.4 | m 1 H |
| | δ 3.3-4.1 | m 4 H |
| | δ 2.4-3.2 | m 9 H |
| | δ 1.8-2.4 | m 4 H |

EXAMPLE 6

(S)-N-methyl-N-[1-phenyl-2-(pyrrolidin-1-yl)]ethyl-o-nitrophenylacetamide hydrochloride hemihydrate 800 mg of (S)-N-methyl-1-phenyl-2-(1-pyrrolidinyl) ethanamine (3.92 mmoles) and 800 mg. of 2-nitrophenylacetic acid (4.42 mmoles) are dissolved in 30 ml of dry methylene chloride. 1.5 g. of dicyclohexylcarbodiimide (7.30 mmoles), dissolved in the minimum amount of methylene chloride, are dropped into this solution kept 0°-5° C. The reaction mixture is allowed to come to room temperature, stirred for 6 hours and left at rest overnight. The precipitated dicyclohexylurea is filtered off and the solution evaporated in-vacuo to dryness.

The residual oil is treated with 50 ml of 10% citric acid and 50 ml of ethyl acetate. A small amount of precipitated solid is filtered off and the two phases are separated. The organic solution is descarded, while the citric one is treated with 36% NaOH solution to basic pH. The basic solution is exhaustively extracted with ethyl acetate, which is dried on sodium sulphate and evaporated to dryness.

The oily residue is dissolved in 30 ml of acetone and the solution brought to slightly acidic pH with HCl/diethyl ether.

The precipitate is filtered, washed with acetone and dried.

Yield: 550 mg. $C_{21}H_{27}ClN_3O_{3.5}$; M.P.=272°-275° C.; M.W.=412.899; $[\alpha]_D^{20}=+98.33$ (C=1, MeOH).

Elemental analysis: Calcd. C, 61.08; H, 6.59; N, 10.18; Cl, 8.59; Found C, 61.20; H, 6.43; N, 9.87; Cl, 8.38.

I.R. (KBr): 1650 $cm^{-1}$ (s); 1525 $cm^{-1}$ (s).

EXAMPLE 7

(S)-N-methyl-N-(1-phenyl-2-dimethylamino)ethyl-o-nitrophenylacetamide hydrochloride hemihydrate 800 mg. of (S)-N$_1$, N$_2$, N$_2$-trimethyl-1-phenyl ethanediamine (4.50 mmoles) and 900 mg. of 2-nitrophenylacetic acid (5.0 mmoles) are dissolved in 30 ml of dry methylene chloride. 1.7 g. of dicyclohexylcarbodiimide (8.25 mmoles), dissolved in 10 ml of methylene chloride, are dropped into this solution kept at 0° C. The reaction mixture is allowed to come to room temperature, stirred for 6 hours and left at rest overnight. The precipitated dicyclohexylurea is filtered off and the solution evaporated in-vacuo to dryness.

The residual oil is treated with 50 ml of 10% citric acid and 50 ml of ethyl acetate. A small amount of precipitated solid is filtered off and the two phases are separated. The organic solution is descarded, while the citric one is treated with 36% NaOH solution to basic pH. The basic solution is exhaustively extracted with ethyl acetate which is dried on sodium sulphate and evaporated to dryness. The oil residue is dissolved in 30 ml or acetone and the solution brought to slightly acidic pH with HCl/diethyl ether. The precipitate is filtered, washed with acetone and dried.

Yield: 300 mg. $C_{19}H_{25}ClN_3O_{3.5}$; M.P.=282°-283° C.; M.W.=386.871; $[\alpha]_D^{20}=+27.23$ (C=1, MeOH).

I.R. (KBr): 1645 $cm^{-1}$ (s); 1525 $cm^{-1}$ (s)

EXAMPLE 8

(S)-N-methyl-N-[1-phenyl-2-(pyrrolidin-1-yl)]ethyl-m-nitrophenylacetamide hydrochloride 1.5 g. of (S)-N-methyl-1-phenyl-2-(1-pyrrolidinyl) ethanamine (7.34 mmoles) and 1.5 g. of 3-nitrophenylacetic acid (8.30 mmoles) are dissolved in 50 ml of dry methylene chloride. 2.6 g. of dicyclohexylcarbodiimide (12.60 mmoles), dissolved in 10 ml of methylene chloride, are dropped into this solution kept at 0° C. The reaction mixture is allowed to come to room temperature, stirred for 6 hours and left at rest overnight. The precipitated dicyclohexylurea is filtered off and the solution evaporated in-vacuo to dryness.

The residual oil is treated with 70 ml of 10% citric acid and 70 ml of ethyl acetate. A small amount of precipitated solid is filtered off and two phases are separated. The organic solution is discarded, while the citric one is treated with 36% NaOH solution to basic pH. The basic solution is exhaustively extracted with ethyl acetate, which is dried on sodium sulphate and evaporated to dryness. The oily residue is dissolve in 50 ml of acetone and the solution brought to slightly acidic pH with HCl/diethyl ether. The precipitate is filtered, washed with acetone and dried.

Yield 700 mg. $C_{21}H_{26}ClN_3O_3$; M.P.=281°-284° C.; M.W.=403.899; $[\alpha]_D^{20}=+104.16$ (C=1, MeOH).

Elemental analysis: Calcd. C, 62.44; H, 6.49; N, 10.40; Cl, 8.78; Found C, 62.19; H, 6.53; N, 10.18; Cl, 8.83.

I.R. (KBr): 1650 $cm^{-1}$ (s); 1525 $cm^{-1}$ (s)

| $^1$H N.M.R. (CDCl$_3$): | δ 12.2 | s 1 H |
|---|---|---|
| | δ 7.1-8.2 | m 9 H |
| | δ 6.4 | dd 1 H |
| | δ 4.1 | AB system, J=16 Hz, 2 H |
| | δ 3.7-4.5 | m 3 H |
| | δ 2.9 | s 3 H |
| | δ 2.6-3.3 | m 3 H |
| | δ 1.7-2.5 | m 4 H |

EXAMPLE 9

(S)-N-methyl-N-(1-phenyl-2-dimethylamino)ethyl-m-nitrophenylacetamide hydrochloride 1.5 g. of (S)-N$_1$,N$_2$,N$_2$-trimethyl-1-phenyl ethanediamine (8.40 mmoles) and 1.6 g. of 3-nitrophenylacetic acid (8.80 mmoles) are dissolved in 50 ml of dry methylene chloride.

3.1 g. of dicyclohexylcarbodiimide (15.0 mmoles), dissolved in 10 ml of methylene chloride, are dropped into this solution, kept at 0° C.

The reaction mixture is allowed to come to room temperature, stirred for 6 hours and left at rest overnight.

The precipitated dicyclohexylurea is filtered off and the solution evaporated in-vacuo to dryness.

The residual oil is treated with 50 ml of 10% citric acid and 50 ml of ethyl acetate. A small amount of precipitated solid is filtered off and the two phases are separated. The organic solution is descarded, while the citric one is treated with 36% NaOH solution to basic pH. The basic solution is exhaustively extracted with ethyl acetate, which is dried on sodium sulphate and evaporated to dryness. The oily residue is dissolved in 30 ml of acetone and the solution brought to slightly acidic pH with HCl/diethyl ether. The precipitate is filtered, washed with acetone and dried.

Yield 600 mg. $C_{19}H_{24}ClN_3O_3$; M.P.=264°–266° C.; M.W.=377.863; $[\alpha]_D^{20}$=+66.13 (C=1, MeOH).

Elemental analysis: Calcd. C, 60.39; H, 6.40; N, 11.12; Cl, 9.38; Found C, 60.24; H, 6.42; N, 10.99; Cl, 9.24.

I.R. (KBr): 1655 cm$^{-1}$ (s); 1530 cm$^{-1}$ (s).

EXAMPLE 10

(S)-N-methyl-N-[1-phenyl-2-(pyrrolidin-1-yl)]ethyl-p-nitrophenylacetamide hydrochloride 1.5 g. of (S)-N-methyl-1-phenyl-2-(1-pyrrolidinyl) ethanamine (7.34 mmoles) and 1.6 g. of 4-nitrophenylacetic acid (8.84 mmoles) are dissolved in 50 ml of dry methylene chloride. 2.7 g. of dicyclohexylcarbodiimide (13.10 mmoles), dissolved in the minimum amount of methylene chloride, are dropped into this solution kept at 0° C.

The reaction mixture is allowed to come to room temperature, stirred for 6 hours and left at rest overnight. The precipitated dicyclohexylurea is filtered off and the solution evaporated in-vacuo to dryness.

The residual oil is treated with 50 ml of 10% citric acid and 50 ml of ethyl acetate. A small amount of precipitated solid is filtered off and the two phases are separated. The organic solution is descarded, while the citric one is treated with 36% NaOH solution to basic pH. The basic solution is exhaustively extracted with ethyl acetate, which is dried on sodium sulphate and evaporated to dryness.

The oily residue is dissolved in 30 ml of acetone and the solution brought to slightly acidic pH with HCl/diethyl ether. The precipitate is filtered, washed with acetone and dried.

Yield 700 mg. $C_{21}H_{26}ClN_3O_3$; M.P.=268°–272° C.; M.W.=403.899; $[\alpha]_D^{20}$=+100.38 (C=1, MeOH).

Elemental analysis: Calcd. C, 62.44; H, 6.49; N, 10.40; Cl, 8.78; Found C, 62.58; H, 6.54; N, 10.42; Cl, 8.58.

I.R. (KBr): 1655 cm$^{-1}$ (s); 1520 cm$^{-1}$ (s).

| $^1$H N.M.R. (CDCl$_3$): | δ 12.1 | s 1 H |
| --- | --- | --- |
| | δ 7.0–8.2 | m 9 H |
| | δ 6.4 | dd 1 H |
| | δ 4.1 | AB system, J=16 Hz, 2 H |
| | δ 3.7–4.2 | m 3 H |
| | δ 2.95 | s 3 H |
| | δ 2.7–3.3 | m 3 H |
| | δ 1.9–2.5 | m 4 H |

EXAMPLE 11

(S)-N-methyl-N-(1-phenyl-2-dimethylamino)ethyl-p-nitrophenylacetamide hydrochloride monohydrate 1.5 g. of (S)-N$_1$,N$_2$,N$_2$-trimethyl-1-phenyl ethanediamine (8.40 mmoles) and 1.6 g. of 4-nitrophenylacetic acid (8.80 mmoles) are dissolved in 50 ml of dry methylene chloride.

b 3.1 g. of dicyclohexylacarbodiimide (15.0 mmoles), dissolved in 10 ml of methylene chloride, are dropped into this solution, kept at 0° C. The reaction mixture is allowed to come to room temperature, stirred for 6 hours and left at rest overnight.

The precipitated dicyclohexylurea is filtered off and the solution evaporated in-vacuo to dryness.

The residual oil is treated with 50 ml of 10% citric acid and 50 ml of ethyl acetate. A small amount of precipitated solid is filtered off and the two phases are separated. The organic solution is descarded, while the citric one is treated with 36% NaOH solution to basic pH. The basic solution is extracted with ethyl acetate, which is dried on sodium sulphate and evaporated to dryness. The oily residue is dissolved in 30 ml of acetone and the solution brought to acidic pH with HCl/diethyl ether.

The precipitate is filtered, washed and dried.

Yield 600 mg. $C_{19}H_{26}ClN_3O_4$; M.P.=263°–265° C.; M.W.=395.879; $[\alpha]_D^{20}$=+24.20 (C=1, MeOH).

Elemental analysis: Calcd. C, 57.64; H, 6.62; N, 10.61; Cl, 8.95; Found C, 58.45; H, 6.41; N, 10.54; Cl, 8.96.

I.R. (KBr): 1660 cm$^{-1}$ (s); 1525 cm$^{-1}$ (s).

EXAMPLE 12

(S)-N-methyl-N-[1-phenyl-2-(pyrrolidin-1-yl)]ethyl-p-trifluoromethylphenylacetamide hydrochloride 1.5 g. of (S)-N-methyl-1-phenyl-2-(1-pyrrolidinyl) ethanamine (7.34 mmoles) and 1.7 g. of 4-trifluoromethylphenylacetic acid (8.34 mmoles) are dissolved in 50 ml of dry methylene chloride. 2.6 g. of dicyclohexylcarbodiimide (12.60 mmoles), dissolved in 10 ml of methylene chloride are dropped into this solution kept at 0° C. The reaction mixture is allowed to come to room temperature, stirred for 6 hours and left at rest overnight.

The precipitated dicyclohexylurea is filtered off and the solution is evaporated in-vacuo to dryness.

The residual oil is chromatographed on silica gel, eluting with CH$_2$Cl$_2$/0.5–2% of MeOH, to afford 1.0 g. of the pure product, which is dissolved in 30 ml of ethyl acetate and the solution brought to acidic pH with HCl/diethyl ether.

The precipitate is filtered, washed and dried.

Yield 800 mg. $C_{22}H_{26}ClF_3N_2O$; M.P.=222°–224° C.; M.W.=426.901; $[\alpha]_D^{20}$=+16.60 (C=1, MeOH).

Elemental analysis: Calcd. C, 61.89; H, 6.14; N, 6.56; Cl, 8.31; F, 13.35; Found C, 61.62; H, 6.24; N, 6.43; Cl, 8.32; F, 13.36.

I.R. (KBr): 1650 cm$^{-1}$ (s); 1320 cm$^{-1}$ (s).

EXAMPLE 13

(S)-N-methyl-N-(1-phenyl-2-dimethylamino)ethyl-p-trifluoromethylphenylacetamide hydrochloride 1.5 g. of (S)-N$_1$,N$_2$,N$_2$-trimethyl-1-phenyl ethanediamine (8.40 mmoles) and 1.9 g. of 4-trifluoromethylphenylacetic acid (9.31 mmoles) are dissolved in 50 ml of dry methylene chloride.

3.2 g. of dicyclohexylcarbodiimide (15.53 mmoles), dissolved in 10 ml of methylene chloride are dropped into this solution kept at 0° C. The reaction mixture is allowed to come to room temperature, stirred for 6 hours and left at rest overnight. The precipitated dicyclohexylurea is filtered off and the solution is evaporated in-vacuo to dryness.

The residual oil is chromatographed on silica gel, eluting with CH$_2$Cl$_2$/0.5–2% of MeOH, to afford 900 mg. of the pure product, which is dissolved in 30 ml of ethyl acetate and the solution brought to acidic pH with HCl/diethyl ether. The precipitate is filtered, washed and dried.

Yield 700 ml; $C_{20}H_{24}ClF_3N_2O$; M.P.=221°–223° C.; M.W.=400.865; $[\alpha]_D^{20}=+41.00$ (C=1, MeOH).

Elemental analysis: Calcd. C, 59.92; H, 6.03; N, 6.99; Cl, 8.85; F, 14.22; Found C, 59.18; H, 6.10; N, 6.88; Cl, 8.74; F, 14.47.

I.R. (KBr): 1655 cm$^{-1}$ (s); 1325 cm$^{-1}$ (s).

EXAMPLE 14

(S)-N-methyl-N-[1-phenyl-2-(pyrrolidin-1-yl)]ethyl-m-trifluoromethylphenylacetamide hydrochloride 1.2 g. of (S)-N-methyl-1-phenyl-2-(1-pyrrolidinyl)ethanamine (5.88 mmoles) and 1.4 g. of 3-trifluoromethylphenylacetic acid (6.86 mmoles) are dissolved in 40 ml of dry methylene chloride.

2.6 g. of dicyclohexylcarbodiimide (12.60 mmoles), dissolved in 10 ml of methylene chloride are dropped into this solution kept at −5° C. The reaction mixture is allowed to come to room temperature, stirred for 6 hours and left at rest overnight. The precipitated dicyclohexylurea is filtered off and the solution is evaporated in-vacuo to dryness.

The residual oil is chromatographed on silica gel eluting with $CH_2Cl_2$/0.5-2% of MeOH, to afford 1.3 g. of the pure product, which is dissolved in 30 ml of ethyl acetate and the solution brought to acidic pH with HCl/diethyl ether.

The precipitate is filtered, washed and dried.

Yield 1.2 g. $C_{22}H_{26}ClF_3N_2O$; M.P.=238°–240° C.; M.W.=426.901; $[\alpha]_D^{20}=+47.5$ (C=1, MeOH).

Elemental analysis: Calcd. C, 61.89; H, 6.14; N, 6.56; Cl, 8.31; F, 13.35; Found C, 61.73; H, 6.24; N, 6.46; Cl, 8.20; F, 13.23.

I.R. (KBr): 1660 cm$^{-1}$ (S); 1340 cm$^{-1}$ (S).

EXAMPLE 15

(S)-N-methyl-N-(1-phenyl-2-dimethylamino)ethyl-m-trifluoromethylphenylacetamide hydrochloride 1.0 g. of (S)-$N_1$, $N_2$, $N_2$-trimethyl-1-phenyl ethanediamine (5.62 mmoles) and 1.4 g. of 3-trifluoromethylphenylacetic acid (6.86 mmoles) are dissolved in 40 ml of dry methylene chloride.

2.4 g. of dicyclohexylcarbodiimide (11.65 mmoles), dissolved in 10 ml of methylene chloride are dropped into this solution kept at −5° C. The reaction mixture is allowed to come to room temperature, stirred for 6 hours and left at rest overnight.

The precipitated dicyclohexylurea is filtered off and the solution is evaporated in-vacuo to dryness.

The residual oil is cromatographed on silica gel, eluting with $CH_2Cl_2$/0.5-2% of MeOH, to afford 1 g. of the pure product, which is dissolved in 30 ml of ethyl acetate and the solution brought to acidic pH with HCl/diethyl ether.

The precipitate is filtered, washed and dried.

Yield 1.0 g. $C_{20}H_{24}ClF_3N_2O$; M.P.=223°–225° C.; M.W.=400.865; $[\alpha]_D^{20}=+23.5$ (C=1, MeOH).

Elemental analysis: Calcd. C, 59.92; H, 6.03; N, 6.99; Cl, 8.85; F, 14.22. Found C, 59.99; H, 6.07; N, 6.97; Cl, 8.88; F, 14.30.

I.R. (KBr): 1665 cm$^{-1}$ (S); 1340 cm$^{-1}$ (S).

1,2 g. of (S)-N-methyl-1-phenyl-2-(1-pyrrolidinyl) ethanamine (5.88 mmoles) and 1,4 g. of 5,6,7,8-tetrahydro-2-naphthylacetic acid (7.36 mmoles) are disclosed in 40 ml of dry methylene chloride.

2,5 g. of dicyclohexylcarbodiimide (12,50 mmoles), dissolved in 10 ml of methylene chloride are dropped into this solution kept at −5° C. The reaction mixture is allowed to come to room temperature, stirred for 6 hours and left at rest overnight.

The precipitated dicyclohexylurea is filtered off and the solution is evaporated in-vacuo to dryness.

The residual oil is chromatographed on silica gel eluting with $CH_2Cl_2$/0.5-2% of MeOH, to afford 1.1 g. of the pure product, which is dissolved in 30 ml of acetone and the solution brought to acidic pH with HCl/diethyl ether.

The precipitate is filtered, washed and dried.

Yield 700 mg $C_{25}H_{33}ClN_2O$ M.P.=217°–219° C. M.W.=412.987 $[\alpha]_D^{20}=+9.4$ (C=1, MeOH)

Elemental analysis: Calcd. C, 72.70; H, 8.05; N, 6.78; Cl, 8.59; Found C, 72.26; H, 8.16; N, 6.62; Cl, 8.44.

I.R. (Kbr): 1655 cm$^{-1}$ (S).

1.1 g. of (S)-$N_1$,$N_2$,$N_2$-trimethyl-1-phenyl ethanediamine(6.18 mmoles) and 1.4 g. of 5,6,7,8-tetrahydro-2-naphtylacetic acid (7,36 mmoles) are dissolved in 40 ml of dry methylene chloride.

2.6 g. of dicyclohexylcarbodiimide (12.60 mmoles), dissolved in 10 ml of methylene chloride are dropped into this solution kept at −5° C.

The reaction mixture is allowed to come to room temperature, stirred for 6 hours and left at rest overnight.

The precipitated dicyclohexylurea is filtered off and the solution is evaporated in-vacuo to dryness.

The residual oil is chromatographed on silica gel, eluting with $CH_2Cl_2$/0.5-2% of MeOH, to afford 1.1 g. of the pure product, which is dissolved in 30 ml of acetone and the solution brought to acidic pH with HCl/diethyl ether.

The precipitate is filtered, washed and dried.

Yield 900 mg $C_{23}H_{31}ClN_2O$ M.P.=229°–230° C. M.W.=386,951 $[\alpha]_D^{20}=+5.6$ (C=1, MeOH)

Elemental analysis: Calcd. C, 71,39; H, 8.08; N, 7.24; Cl 9.16; Found C, 71.35; H, 8.03; N, 7.23; CL 9.16.

I.R. (KBr): 1635 cm$^{-1}$ (S).

TABLE I

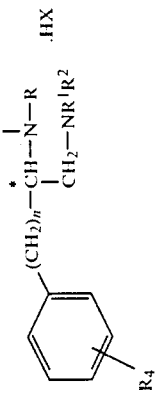

| Example No. | n | R | R₁ R₂ | R₃ | R₄ | HX | MOLECULAR FORMULA | MOLECULAR WEIGHT | MELTING POINT | $[\alpha]_D^{20}$ (C = 1, MeOH) | CONFIG. AT THE ASYM. C ATOM |
|---|---|---|---|---|---|---|---|---|---|---|---|
| 1 | 0 | —COCH₂— (3,4-diCl-phenyl) | R₁, R₂ = cyclopentyl | CH₃ | H | HCl | C₂₁H₂₅Cl₃N₂O | 427.798 | 240° C. | +23.64 | S |
| 2 | 0 | —COCH₂— (3,4-diCl-phenyl) | R₁ = R₂ = CH₃ | CH₃ | H | HCl | C₁₉H₂₃Cl₃N₂O | 401.761 | 225° C. | +104.77 | S |
| 3 | 0 | —COCH₂— (3,4-diCl-phenyl) | R₁ = R₂ = CH₃ | C₂H₅ | H | HCl | C₂₀H₂₅Cl₃N₂O | 415.787 | 195–200° C. | +70.8 | S |
| 4 | 1 | —COCH₂— (3,4-diCl-phenyl) | R₁ = R₂ = CH₃ | CH₃ | H | HCl | C₂₀H₂₅Cl₃N₂O | 415.787 | 175° C. | −4.65 | S |
| 5 | 1 | —COCH₂— (3,4-diCl-phenyl) | R₁, R₂ = cyclopentyl | CH₃ | H | HCl | C₂₂H₂₇Cl₃N₂O | 441.823 | 187–190° C. | +4.22 | S |

TABLE 1-continued $$\text{(CH}_2)_n-\overset{*}{\text{CH}}-\overset{R^3}{\underset{\text{CH}_2-\text{NR}^1\text{R}^2}{\text{N}-\text{R}}} \cdot \text{HX}$$

(with phenyl ring bearing R₄ substituent)

| Example No. | R | n | R₁, R₂ | R₃ | R₄ | HX | MOLECULAR FORMULA | MOLECULAR WEIGHT | MELTING POINT | $[\alpha]_D^{20}$ (C = 1, MeOH) | CONFIG. AT THE ASYM. C ATOM |
|---|---|---|---|---|---|---|---|---|---|---|---|
| 6 | —COCH₂—(2-NO₂-C₆H₄) | 0 | R₁, R₂ = (cyclic) | CH₃ | H | HCl.½H₂O | C₂₁H₂₇ClN₃O₃.₅ | 412.899 | 272–275° C. | +98.33 | S |
| 7 | —COCH₂—(2-NO₂-C₆H₄) | 0 | R₁ = R₂ = CH₃ | CH₃ | H | HCl.½H₂O | C₁₉H₂₅ClN₃O₃.₅ | 386.871 | 282–283° C. | +27.23 | S |
| 8 | —COCH₂—(3-NO₂-C₆H₄) | 0 | R₁, R₂ = (cyclic) | CH₃ | H | HCl | C₂₁H₂₆ClN₃O₃ | 403.899 | 281–284° C. | +104.16 | S |
| 9 | —COCH₂—(3-NO₂-C₆H₄) | 0 | R₁ = R₂ = CH₃ | CH₃ | H | HCl | C₁₉H₂₄ClN₃O₃ | 377.863 | 264–266° C. | +66.13 | S |
| 10 | —COCH₂—(4-NO₂-C₆H₄) | 0 | R₁, R₂ = (cyclic) | CH₃ | H | HCl | C₂₁H₂₆ClN₃O₃ | 403.899 | 268–272° C. | +100.38 | S |
| 11 | —COCH₂—(4-NO₂-C₆H₄) | 0 | R₁ = R₂ = CH₃ | CH₃ | H | HCl.H₂O | C₁₉H₂₆ClN₃O₄ | 395.879 | 263–265° C. | +24.20 | S |

TABLE I-continued

General structure:

$$\text{Ar}-(CH_2)_n-\overset{*}{\underset{CH_2-NR^1R^2}{CH}}-\overset{R^3}{\underset{}{N}}-R \cdot HX$$

where Ar is a substituted phenyl/naphthyl group with $R_4$ substituent.

| Example No. | Ar | n | R | $R_1, R_2$ | $R_3$ | $R_4$ | HX | MOLECULAR FORMULA | MOLECULAR WEIGHT | MELTING POINT | $[\alpha]_D^{20}$ (C = 1, MeOH) | CONFIG. AT THE ASYM. C ATOM |
|---|---|---|---|---|---|---|---|---|---|---|---|---|
| 12 | 4-CF$_3$-phenyl | 0 | —COCH$_2$— | $R_1, R_2$ = (cyclopentyl ring) | CH$_3$ | H | HCl | C$_{22}$H$_{26}$ClF$_3$N$_2$O | 426.901 | 222–224° C. | +16.60 | S |
| 13 | 4-CF$_3$-phenyl | 0 | —COCH$_2$— | $R_1 = R_2 =$ CH$_3$ | CH$_3$ | H | HCl | C$_{20}$H$_{24}$ClF$_3$N$_2$O | 400.865 | 221–223° C. | +41.00 | S |
| 14 | 3-CF$_3$-phenyl | 0 | —COCH$_2$— | $R_1, R_2$ = (cyclopentyl ring) | CH$_3$ | H | HCl | C$_{22}$H$_{26}$ClF$_3$N$_2$O | 426.901 | 238–240° C. | +47.5 | S |
| 15 | 3-CF$_3$-phenyl | 0 | —COCH$_2$— | $R_1 = R_2 =$ CH$_3$ | CH$_3$ | H | HCl | C$_{20}$H$_{24}$ClF$_3$N$_2$O | 400.865 | 223–225° C. | +23.5 | S |
| 16 | tetrahydronaphthyl | 0 | —COCH$_2$— | $R_1, R_2$ = (cyclopentyl ring) | CH$_3$ | H | HCl | C$_{25}$H$_{33}$ClN$_2$O | 412.987 | 217–219° C. | +9.4 | S |
| 17 | tetrahydronaphthyl | 0 | —COCH$_2$— | $R_1 = R_2 =$ CH$_3$ | CH$_3$ | H | HCl | C$_{23}$H$_{31}$ClN$_2$O | 386.951 | 229–230° C. | +5.6 | S |

The pharmacological activity of the compounds of this invention is illustrated by various in vivo models using the following test procedures, in which the mouse tail flick test demonstrates analgesic activity.

(A) TAIL-FLICK TEST (Modified from the procedure published by D'Amour et al., J. Pharm. Exptl. Ther. 72, 74/1941)

Male Charles River mice, average weight 26 g, are used. Selection is carried out before the beginning of experiments: only mice whose reaction time is less than 8 sec are used. They are randomly distributed into groups of 10 and dosed with compounds under test, with positive and negative controls being included.

Compounds under test administered subcutaneously in isotonic saline in a volume of 20 ml.Kg$^{-1}$. 30 minutes later mice are placed again under heat source (Socrel apparatus) and reaction time is recorded.

The analgesic activity of the test compound is expressed as the percent number of mice doubling the initial time within a group.

$$\% \text{ analgesia} = \frac{\text{No. of mice doubling the reaction time}}{\text{Total No. of mice per group}} \times 100$$

(B) RECEPTOR AFFINITY STUDY

Tissue preparation

Radio receptor binding to $\mu$ and K sites is performed on fresh guinea pig brain homogenate prepared according to Kosterlitz. (1981).

Whole brain without cerebellum is homogenized in 50 mM, Tris-buffer (pH 7.4 at 0° C.) and centrifuged at 49,000×g×10 min.

The pellet is then resuspended in the same buffer, incubated at 37° C. for 45 min. and centrifuged again.

1.9 ml of the final homogenate (1:100 in Tris-pH 7.4, 0° C.) is used for the binding assay.

Binding to $\mu$ sites (Magnan J., 1982)

$^3$H [D-Ala$^2$, MePhe$^4$, Gly-ol$^5$] Enkephalin ($^3$H-DAGO), an enkephalin analogue that binds selectively to $\mu$ receptor, is added to the biological substrate and incubated at 25° C. for 40 min., filtered through Whatman GF-C and washed with ice-cold Tris-buffer.

The filters are then dried, solubilized in Filtercount and the radioactivity monitored. Non specific binding is determined in the presence of 10$^{-6}$M Naloxone.

Binding to K sites (Magnan J., 1982)

The binding of tritiated Ethylketocyclazocine to brain homogenate is measured the in presence of 100 nanomolar D-Ala-D-LeuEnkephalin (DADLE) and 100 nanomolar DAGO, added to saturate the $\delta$ and $\mu$ opioid receptors respectively.

Final homogenate with solutions of the cold ligand and of the labelled ligand is incubated for 40 min. at 25° C., filtered through Whatman GF/C glass filter discs and washed.

The radioactivity bound to the filters is counted by liquid scintillation spectrophotometry.

MR 2266.500 nM is utilized to determine the saturable binding.

For the calculation of the kinetic parameters of the binding of labelled and unlabelled ligands, the equilibrium dissociation constant ($K_D$), the inhibition constant ($K_i$) and the maximum number of binding sites (B max) are determined from saturation curves and competition experiments (Hill 1910; Scatchard 1949; Cheng and Prusoff 1973; Gillan et al. 1980).

A concentration of radioligand near $K_D$ is used in the binding assays evaluating our compounds.

Hill, A. V. (1910) : J. Physiol.40, IV-VIII (1910)
Scatchard G. (1949): Ann. N.Y. Acad.Sci., 51, 660–674
Cheng and Prusoff W. H.(1973) : Biochem. Pharmac.22, 3099–3102
Gillan M. G. C., Kosterlitz H. W. :Br.J. Pharmac. 70, and Paterson S. Y. (1980) 481–490
Kotsterliz H. W., Paterson S. Y. :Br.J. Pharmac. 73, and Robson L. E. (1981) 939–949
Magnan J., Paterson S. Y., :Arch. Pharmacol. 319, Tavani A., and Kosterlits 197–205 H. W. (1982)

The results of the test procedures are shown in Table II.

TABLE II

| Example No. | MOUSE TAIL-FLICK ED$_{50}$ (mg./kg.) SUBCUTANEOUS | OPIATE RECEPTORS BINDING | |
|---|---|---|---|
| | | kappa $K_i$ = nM | mu |
| 1 | 0.022 | 0.77 | 124 |
| 2 | 0.1 | 2.01 | 518 |
| 3 | 0.28 | 4.79 | 874 |
| 4 | 9.09 | >100 | |
| 5 | >10 | >100 | |
| 6 | 3.5 | 3.56 | 1219 |
| 7 | 5.0 | 14.5 | >1000 |
| 8 | 0.036 | 0.49 | 194 |
| 9 | 0.13 | 1.29 | 1054 |
| 10 | 0.036 | 1.29 | 100 |
| 11 | 0.4 | 7.89 | 544 |
| 12 | 0.030 | 1.90 | 500 |
| 13 | 0.39 | 3.20 | >1000 |
| 14 | 0.097 | | |
| 15 | 0.187 | | |
| 16 | 0.149 | | |
| 17 | 0.412 | | |

What is claimed is:

1. A compound of formula (I):

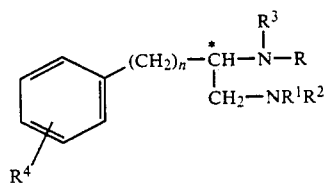

or a pharmaceutically acceptable salt or solvate thereof, wherein
R has the formula

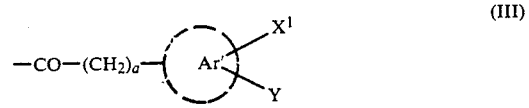

wherein Ar' represents a phenyl group; X$^1$ and Y each independently represent hydrogen; C$_{1-12}$ alkyl; phenyl, phenyl(C$_{1-12}$)alkyl, naphthyl or naphthyl-(C$_{1-12}$)alkyl unsubstituted or substituted in the phenyl or naphthyl moiety by halogen, C$_{1-6}$ alkyl, phenyl, C$_{1-6}$ alkoxy, halo(C$_{1-6}$)alkyl, hydroxy, amino, nitro, carboxy, C$_{1-6}$-alkoxycarbonyl, C$_{1-6}$ alkoxycarbonyl-C$_{1-6}$ alkoxycarbonyl-(C$_{1-6}$)-alkyl, C$_{1-6}$ alkylcarbonyloxy or C$_{1-6}$ alkylcarbonyl; hydroxy; C$_{1-12}$-alkoxy; halogen; trifluoromethyl; nitro; cyano; or —SO$_3$H, —SO$_2$NR$^7$R$^8$, $CO_2R^7$, $-COR^7$ or $-CONR^7R^8$, wherein $R^7$ and $R^8$ are independently hydrogen, $C_{1-12}$ alkyl, unsubstituted phenyl or naphthyl or phenyl or naphthyl substituted by halogen, $C_{1-6}$ alkyl, phenyl, $C_{1-6}$ alkoxy, halo($C_{1-6}$) alkyl, hydroxy, amino, nitro carboxy, $C_{1-6}$ alkoxycarbonyl, $C_{1-6}$ alkoxycarbonyl-($C_{1-6}$)-alkyl, $C_{1-6}$ alkylcarbonyloxy or $C_{1-6}$ alkylcarbonyl; or $X^1$ together with Y form a cycloalkylene ring of up to 12 carbon atoms; and a represents an integer 1, 2, or 3;

$R^1$ together with $R^2$ forms pyrrolidinyl;

$R^3$ represents hydrogen or $C_{1-12}$ alkyl;

$R^4$ represents hydrogen, halogen, $C_{1-12}$ alkyl, hydroxy, $C_{1-12}$ alkoxy, nitrile, nitro or amino; and n represents 0.

2. A compound according to claim I, wherein a is 1 and $Ar^1$, $X^1$ and Y are

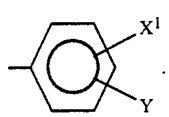

3. A compound according to claim 1, wherein X' and Y each independently represent hydrogen, halogen, trifluoromethyl or nitro;

$R^3$ represents hydrogen or $C_{1-6}$ alkyl;

$R^4$ represents hydrogen, halogen, $C_{1-6}$ alkyl, hydroxy, $C_{1-6}$ alkoxy, nitrile or amino; and n is O.

4. A compound selected from the group consisting
(S) N-methyl-N-[1-phenyl-2-(pyrrolidin-1-yl)]ethyl-3,4-dichlorophenylacetamide hydrochloride;
(S) N-methyl-N-[[1-(pyrrolidin-1-yl)-3-phenyl]prop-2-yl]-3,4-dichlorophenylacetamide hydrochloride;
(S)-N-methyl-N-[1-phenyl-2-(pyrrolidin-1-yl)]ethyl-o-nitrophenylacetamide hydrochloride hemihydrate;
(S)-N-methyl-N-[1-phenyl-2-(pyrrolidin-1-yl)]ethyl-m-nitrophenylacetamide hydrochloride;
(S) N-methyl-N-[1-phenyl-2-(pyrrolidin-1-yl)]ethyl-p-nitrophenylacetamide hydrochloride;
(S) N-methyl-N-[1-phenyl-2-(pyrrolidin-1-yl)]ethyl-p-trifluoromethylphenylacetamide hydrochloride;
(S) N-methyl-N-[1-phenyl-2-(pyrrolidin-1-yl)]ethyl-m-trifluoromethylphenylacetamide hydrochloride.

5. An analgesic pharmaceutical composition, which comprises an analgesically effective amount of a compound of formula (I):

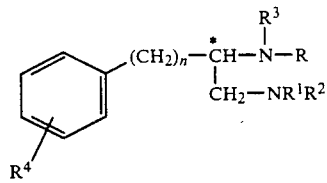

or a pharmaceutically acceptable salt or solvate thereof, wherein

R has the formula

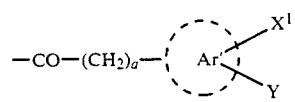

wherein Ar' represents a phenyl group; $X^1$ and Y each independently represent hydrogen; $C_{1-12}$ alkyl; phenyl, phenyl($C_{1-12}$)alkyl, naphthyl or naphthyl-($C_{1-12}$)alkyl unsubstituted or substituted in the phenyl or naphthyl moiety by halogen, $C_{1-6}$ alkyl, phenyl, $C_{1-6}$ alkoxy, halo($C_{1-6}$)alkyl, hydroxy, amino, nitro, carboxy, $C_{1-6}$-alkoxycarbonyl, $C_{1-6}$ alkoxycarbonyl-($C_{1-6}$)-alkyl, $C_{1-6}$ alkylcarbonyloxy or $C_{1-6}$ alkylcarbonyl; hydroxy; $C_{1-12}$-alkoxy; halogen; trifluoromethyl; nitro; cyano; or $-SO_3H$, $-SO_2NR^7R^8$, $-CO_2R^7$, $COR^7$ or $-CONR^7R^8$, wherein $R^7$ and $R^8$ are independently hydrogen, $C_{1-12}$ alkyl, unsubstituted phenyl or naphthyl or phenyl or naphthyl substituted by halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl, ($C_{1-6}$)-alkylcarbonyloxy or $C_{1-6}$ alkylcarbonyl; or $X^1$ together with Y form a cycloakylene ring of up to 12 carbon atoms; and a represents an integer 1, 2, or 3;

$R^1$ together with $R^2$ forms pyrrolidinyl;

$R^3$ represents hydrogen or $C_{1-12}$ alkyl;

$R^4$ represents hydrogen, halogen, $C_{1-12}$ alkyl, hydroxy, $C_{1-12}$ alkoxy, nitrile, nitro or amino; and n represents O; in combination with a pharmaceutically acceptable carrier.

6. The composition according to claim 5, in unit dosage form.

7. The composition according to claim 5, wherein a is 1 and $Ar^1$, $X^1$ and Y are

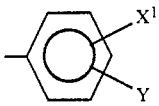

8. The composition according to claim 5, wherein $X^1$ and Y each independently represent hydrogen, halogen, trifluoromethyl or nitro;

$R^3$ represents hydrogen or $C_{1-6}$ alkyl;

$R^4$ represents hydrogen, halogen, $C_{1-6}$ alkyl, hydroxy, $C_{1-6}$ alkoxy, nitrile or amino; and n is O.

9. The composition according to claim 5, wherein said compound is selected from the group consisting of:
(S)-N-methyl-N-[1-phenyl-2-(pyrrolidin-1-yl)]ethyl-3,4-dichlorophenylacetamide hydrochloride;
(S)-N-methyl-N-[[1-(pyrrolidin-1yl)-3-phenyl]prop-2-yl]-3,4-dichlorophenylacetamide hydrochloride;
(S)-N-methyl-N-[1-phenyl-2-(pyrrolidin-1-yl)]ethyl-o-nitrophenylacetamide hydrochloride hemihydrate;
(S)-N-methyl-N-[1-phenyl-2-(pyrrolidin-1-yl)]ethyl-m-nitrophenylacetamide hydrochloride;
(S)-N-methyl-N-[1-phenyl-2-(pyrrolidin-1-yl)]ethyl-p-nitrophenylacetamide hydrochloride;
(S)-N-methyl-N-[1-phenyl-2-(pyrrolidin-1-yl)]ethyl-p-trifluoromethylphenylacetamide hydrochloride; and
(S)-N-methyl-N-[1-phenyl-2-(pyrrolidin-1-yl)]ethyl-m-trifluoromethylphenylacetamide hydrochloride.

10. A method of treating pain in mammals, which comprises administering to a mammal in need thereof an analgesically effective amount of a compound of formula (I):

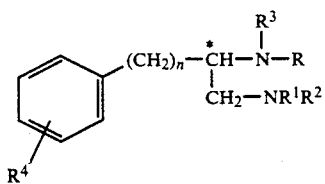

or a pharmaceutically acceptable salt or solvate thereof, wherein R has the formula

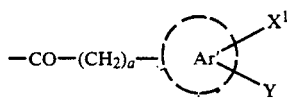

wherein Ar' represents a phenyl group; $X^1$ and Y each independently represent hydrogen; $C_{1-12}$ alkyl; phenyl, phenyl($C_{1-12}$)alkyl, naphthyl or naphthyl ($C_{1-12}$)alkyl unsubstituted or substituted in the phenyl or naphthyl moiety by halogen, $C_{1-6}$ alkyl, phenyl, $C_{1-6}$ alkoxy, halo($C_{1-6}$)alkyl, hydroxy, amino, nitro, carboxy, $C_{1-6}$-alkoxycarbonyl, $C_{1-6}$ alkoxycarbonyl-($C_{1-6}$)-alkyl, $C_{1-6}$ alkylcarbonyloxy or $C_{1-6}$ alkylcarbonyl; hydroxy; $C_{1-12}$-alkoxy; halogen; trifluoromethyl; nitro; cyano; or $-SO_3H$, $-SO_2NR^7R^8$, $-CO_2R^7$, $-COR^7$ or $-CONR^7R^8$, wherein $R^7$ and $R^8$ are independently hydrogen, $C_{1-12}$ alkyl, unsubstituted phenyl or naphthyl or phenyl or naphthyl substituted by halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl, $C_{1-6}$ alkylcarbonyloxy or $C_{1-6}$ alkylcarbonyl; or $X^1$ together with Y form a cycloakylene ring of up to 12 carbon atoms; and a represents an integer 1, 2, or 3;

$R^1$ together with $R^2$ forms pyrrolidinyl;

$R^3$ represents hydrogen or $C_{1-12}$ alkyl;

$R^4$ represents hydrogen, halogen, $C_{1-12}$ alkyl, hydroxy, $C_{1-12}$ alkoxy, nitrile, nitro or amino; and n represents O.

11. A method according to claim 10, wherein a is 1 and $Ar^1$, $X^1$ and Y are

12. A method according to claim 10, wherein $X^1$ and Y each independently represent hydrogen, halogen, trifluoromethyl or nitro;

$R^3$ represents hydrogen or $C_{1-6}$ alkyl;

$R^4$ represents hydrogen, halogen, $C_{1-6}$ alkyl, hydroxy, $C_{1-6}$ alkoxy, nitrile or amino; and n is O.

13. A method according to claim 10, wherein said compound is selected from the group consisting of:

(S)-N methyl-N-[1-phenyl-2-(pyrrolidin-1-yl)]ethyl-3,4-dichlorophenylacetamide hydrochloride;

(S)-N-methyl-N-[[1-(pyrrolidin-1yl)-3-phenyl]prop-2-yl]-3,4-dichlorophenylacetamide hydrochloride;

(S)-N-methyl-N-[1-phenyl-2-(pyrrolidin-1-yl)]ethyl-o-nitrophenylacetamide hydrochloride hemihydrate;

(S)-N-methyl-N-[1-phenyl-2-(pyrrolidin-1-yl)]ethyl-m-nitrophenylacetamide hydrochloride;

(S)-N-methyl-N-[1-phenyl-2-(pyrrolidin-1-yl)]ethyl-p-nitrophenylacetamide hydrochloride;

(S)-N-methyl-N-[1-phenyl-2-(pyrrolidin-1-yl)]ethyl-p-trifluoromethylphenylacetamide hydrochloride; and (S)-N-methyl-N-[1-phenyl-2-(pyrrolidin-1-yl)]ethyl-m-trifluoromethylphenylacetamide hydrochloride.

* * * * *